United States Patent [19]
Geerts et al.

[11] Patent Number: 5,993,845
[45] Date of Patent: Nov. 30, 1999

[54] ANTI-FIBROTIC MEDICAMENT

[75] Inventors: Albert Emmanuel Corneille Geerts, Brussels; Toshiro Niki, Wemmel, both of Belgium

[73] Assignee: Vrije Universiteit Brussel, Belgium

[21] Appl. No.: 08/922,338

[22] Filed: Sep. 3, 1997

[30] Foreign Application Priority Data

Sep. 4, 1996 [EP] European Pat. Off. .............. 96202460

[51] Int. Cl.$^6$ ....................................................... A61F 2/02
[52] U.S. Cl. ............................................................ 424/423
[58] Field of Search ............................................ 424/423

[56] References Cited

FOREIGN PATENT DOCUMENTS

WO9404671  3/1994  WIPO .

OTHER PUBLICATIONS

M. Yoshida et al., "Reversible Arrest of Proliferation of Rat 3Y1 Fibroblasts in Both the G1 and G2 Phases by Trichostatin A," *Experimental Cell Research*, 177(1988) 122–131.

M. Yoshida et al., "Potent and Specific Inhibition of Mammalian Histone Deacetylase both in Vivo and in Vitro by Trichostatin A," *J. Biological Chemistry*, vol. 265, No. 28 (1990) 17174–17179.

M. Kijima et al., "Trapoxin, an Antitumor Cyclic Tetrapeptide, Is an Irreversible Inhibitor of Mammalian Histone Deacetylase," *J. Biological Chemistry*, vol. 268, No. 30 (1993) 22429–22435.

A. Gressner et al., "Effect of n–Butyrate on the Synthesis of Sulfated Glycosaminoglycans and Hyaluronate by Rat Liver Rat–Storing Cells (Ito Cells)," *Biochemical Pharmacology*, vol. 37, No. 19 (1988) 3771–3776.

*Primary Examiner*—Carlos Azpuru
*Attorney, Agent, or Firm*—Banner & Witcoff, Ltd.

[57] ABSTRACT

Compounds of submicromolar concentrations of a histone deacetylase inhibitor, useful as anti-fibrotic agents. The compounds strongly inhibit three main features of myofibroblastic differentiation of cultured hepatic stellate cells and of skin fibroblasts: (1) synthesis of collagens type I and III, the predominant collagens in fibrosis of liver and other organs; (2) cellular proliferation; and (3) expression of smooth muscle α-actin, a marker for activated myofibroblasts. Preferred compounds include trichostatin A or a pharmaceutically acceptable salt thereof, and sodium butyrate.

14 Claims, No Drawings

ANTI-FIBROTIC MEDICAMENT

FIELD OF THE INVENTION

This application is a continuation of European Patent Application No. 9620246.0 filed Sep. 4, 1996.

The invention relates to a pharmaceutical composition for the treatment of fibrosis, for example liver fibrosis, cirrhosis and fibrotic skin diseases such as hypertrophic scars, keloid and Dupuytren's contracture.

DESCRIPTION OF THE RELATED ART

Fibrosis in general is a condition which is characterized by excessive deposition of connective tissue in organs such as skin, lung, hart, liver, parcreas, kidney, etc.

Liver fibrosis is a pathological condition characterized by excessive deposition of connective tissue proteins. Rather than a single disease entity, it is a condition resulting from various diseases, including viral hepatitis, alcoholic liver disease, schistosomiasis, etc. Regardless of the initial cause of the disease, the liver parenchyma is progressively replaced by connective tissue, resulting in deterioration of liver functions.

Skin fibrosis is a pathological condition characterized by excessive deposition of connective tissue proteins in the dermis. Skin fibrosis results of a variety of skin injuries including mechanical trauma, burn wounds, chronic inflammation or chronic auto-immunity. Regardless of the initial cause, the dermis of the skin thickens.

To date, no truly effective therapeutic drug exists for the treatment of fibrotic diseases.

Hepatic stellate cells are the major connective tissue producing cells in both normal and fibrotic livers. In the normal situation, stellate cells serve as vitamin A storage site. These cells are quiescent, show little proliferative activity, and express a limited spectrum of connective tissue proteins. In injured or fibrotic livers, however, stellate cells lose their fat-droplets and change their phenotype into myofibroblast-like cells. These myofibroblast-like cells are "activated" cells, show high proliferative activity, and produce large amounts of collagens and other extracellular matrix proteins. Accordingly, this cell type is the logical target for therapeutic intervention. Compounds with antifibrotic effect on stellate cells will be a promising candidate molecule for the treatment of liver fibrosis and cirrhosis.

Fibroblasts of normal skin are quiescent. They synthesize controlled amounts of connective tissue proteins and have low proliferative activity. Following skin injury, these cells become activated, i.e. they proliferate, express α-smooth muscle actin and synthesize large amounts of connective tissue proteins. The activated cells are often called myofibroblasts.

SUMMARY OF THE INVENTION

According to the invention it was surprisingly found that submicromolar concentrations of a histone deacetylase inhibitor and in particular of trichostatin A strongly inhibit three main features of myofibroblastic differentiation of cultured hepatic stellate cells and of skin fibroblasts:

(1) synthesis of collagens type I and III, the predominant collagens in fibrosis of liver and in many other organs;

(2) cellular proliferation; and (3) expression of smooth muscle α-actin, a marker for differentiated myofibroblasts. These results indicate that trichostatin A is a potent antifibrogenic agent, totally different from any other therapeutic compounds previously described.

The present invention is directed to the use of a histone deacetylase inhibitor or a pharmaceutically acceptable salt thereof for the preparation of a pharmaceutical composition for the treatment of fibrosis.

Currently six compounds as inhibitors of histone deacetylase are known. Histone deacetylase inhibitors are substances causing an inhibition of the activity of histone deacetylases, resulting inhyperacetylation of histones, comprising:

trapoxin trichostatin A, B, C

Na-butyrate apicidin A (cyclic tetrapeptide)

HC-toxin (cyclic tetrapeptide)

chlamydocin.

Sodium butyrate is a natural 4 carbon fatty acid that inhibits histone deacetylase in a non-competitive manner, and requires millimolar concentrations for its biologic activities. Trichostatin A and trapoxin are specific inhibitors of histone deacetylase, and are much more potent than sodium butyrate, being effective in the submicromolar range.

DETAILED DESCRIPTION OF THE INVENTION

The description in this application is in particular directed to trichostatin A as a non-limiting example and is never intended to limit the scope of the invention.

Trichostatin A or derivatives thereof are disclosed to be useful as an antifibrotic agent for the treatment fibrosis. Pharmaceutical formulations and use of compounds of Trichostatin A are also disclosed.

Trichostatin A is an antifungal agent originally isolated from Streptomyces hygroscopicus by Tsuji et al. (J. Antibiot 29:1–6, 1976). Trichostatin A is also useful as an anticancer (Cancer Res 47:3688–3691, 1987) and an antiprotozoal agent (J. Antibiot 41:461–468, 1988). In the course of experiments we discovered that Trichostatin A has a strong antifibrotic effect on hepatic stellate cells which are the major connective tissue producing cells in the liver.

Trichostatin A can be brought in the form of pharmaceutically acceptable salts. As such pharmaceutically acceptable salts may be used so long as they do not adversely affect the desired pharmacological effects of the compounds. The selection and the production can be made by those skilled in the art. For instance, as a pharmaceutically acceptable salt, and alkali metal salt such as sodium salt or a potassium salt, an alkaline earth metal salt such as calcium salt or a magnesium salt, a salt with an organic base such as an ammonium salt, or a salt with an organic base such as a triethylamine salt or an ethanolamine salt, may be used.

Subjects to be treated by the present invention include both humans and animals.

The antifibrotic agent of the present invention may be administered orally or non-orally. In the case of oral administration, it may be administered in the form of soft and hard capsules, tablets, granules, powders, solutions, suspensions or the like. In the case of non-oral administration, they may be administered in the form of ointments or injection solution, drip infusion formulations, suppositories whereby continuous membrane absorption can be maintained in the form of solid, viscous liquid, or suspension. The selection of the method for preparation of these formulations and the vehicles, disintegrators or suspending agents, can be readily made by those skilled in the art. The antifibrotic agent of the present invention may contain a further substance having antifibrotic activities, in addition to Trichostatin A or its pharmaceutically acceptable salts.

The amount of the active ingredients in the composition of the present invention may vary depending on the formulation, but is usually from 0.1 to 50% by weight irrespective of the manner of administration. The dose is determined taking into consideration the age, sex, and symptom of the disease of the subject, the desired therapeutic effect, the period for administration, etc. However, preferably a daily dose of the active ingredient is from 0.05 to 100 mg for an adult.

The following examples are provided to illustrate the present invention, and should not be construed as limiting thereof.

Trichostatin A 7-[4-(dimethylamino)phenyl]-N-hydroxy-4,6-dimethyl-7-oxo-2,4-heptadienamide was prepared from the culture broth of *Streptmyces platensis* No.145. Sodium butyrate was purchased from Sigma (St. Louis, Mo., USA). Stock solutions of Trichostatin A were prepared in ethanol (2 mg/ml), stored at −20° C., and diluted as required for each experiment. The final concentration of ethanol in the medium was 0.0016%. Stock solutions of sodium butyrate (100 mmol/L) were prepared in distilled water, and diluted as required.

EXAMPLE 1

Effect of Trichostatin A and Sodium Butyrate on the Synthesis of Collagens Type I and III, and Smooth Muscle α-actin by Hepatic Stellate Cells The antifibrotic activity of Trichostatin A and sodium butyrate were tested using cultures of hepatic stellate cells.

Stellate cells were isolated from adult Wistar rats (400–550 g) by enzymatic digestion of the liver with collagenase/pronase/DNAase followed by density gradient centrifugation on Nicodenz (Nycomed, Oslo, Norway).

After isolation cells were suspended in Dulbecco's modified Eagle's medium supplemented with 10% fetal calf serum, 100 U/ml penicillin, and 100 μg/ml streptomycin, and cultured at 37° C. in a humidified atmosphere with 5% $CO_2$ and 95% air.

At day 3 cells were exposed to Trichostatin A (1–100 nmol/L) for 24 h. During the subsequent 24 h cells were metabolically labeled with 25 μCi/ml of Trans 35S-label (specific activity of $^{35}$S-methionine>1,000 Ci/mmol, ICN Biomedicals, Costa Mesa Calif.) while exposure to the compounds was continued. After labelling medium was collected, and subjected to immunoprecipitation using antibodies against collagens type I and III and smooth muscle α-actin. The precipitates were fractionated by SDS-PAGE and radioactivity of specific bands were measured by the PhosphorImaging technology. For the effect at mRNA level, cells were exposed to 100 nmol/L Trichostatin A for 24 h. RNA was then extracted and analyzed by Northern hybridization analysis.

Table 1 and 2 show the results which were expressed as percentage value relative to the control culture, respectively for Trichostatin A and sodium butyrate. Note the dose-dependent suppression of collagens type I and III synthesis by Trichostatin A. Also, note the strong suppression of smooth muscle α-actin, an activation marker of stellate cells.

TABLE 1

| Results for Trichostatin A | | | |
|---|---|---|---|
| | 100 nM | 10 nM | 1 nM |
| collagen I | 37.9 ± 5.6 | 68.9 ± 4.7 | 91.7 ± 9.5 |
| collagen III | 30.1 ± 9.6 | 73.2 ± 20.9 | 71.9 ± 21.0 |
| SM α-actin | 15.5 ± 7.4 | 54.4 ± 5.3 | 87.6 ± 0.3 |

Sodium butyrate suppressed smooth muscle α-actin less effectively, with 50% reduction at a concentration of 1 mmol/L. Inhibition of collagen type III and smooth muscle α-actin synthesis indicated that Trichostatin A was more potent than butyrate by 5 orders of magnitude.

TABLE 2

| Results for sodium butyrate | | | |
|---|---|---|---|
| | $10^{-3}$ M | $10^{-4}$ M | $10^{-5}$ M |
| collagen I | 107.8 ± 9.8 | 127.9 ± 16.2 | 92.8 ± 11.7 |
| collagen III | 67.9 ± 19.1 | 90.6 ± 42.2 | 109.4 ± 31.1 |
| SM α-actin | 50.0 ± 19.9 | 91.6 ± 23.4 | 97.9 ± 24.4 |

EXAMPLE 2

Effect of Trichostatin A on the Gene Expression of Collagens Type I and III, and Smooth Muscle α-actin by Hepatic Stellate Cells Hepatic stellate cells were isolated and cultured as described in Example 1. Cells were exposed to 100 nmol/L Trichostatin A for 24 h. RNA was then extracted and analyzed by Northern hybridization analysis.

At day 3 cells were exposed to 100 nmol/L Trichostatin A or 1 mmol/L sodium butyrate for 24 h. Total RNA was extracted by the method of Chomczynski and Sacchi. Northern hybridization was performed using P-labeled cDNA probes for rat procollagen $α_1$ (I) (1.6 kb Pst I fragment), rat procollagen $α_1$ (III) (0.5 kb Hind III/EcoRI fragment), and glyceraldehyde-3-phosphate dehydrogenase (GAPDH) (0.5 kb XbaI/HindIII fragment). For smooth muscle α-actin, a cRNA probe corresponding to the 5'-untranslated region of mouse smooth muscle α-actin mRNA was used as described previously. The results were quantitated by Phosphor-Imaging and corrected for GAPDH.

The results at the mRNA level are shown in Table 3. Collagen type III and smooth muscle α-actin mRNA levels were suppressed to a similar extent as at the protein level. On the other hand, only modest tendency for suppression was observed for collagen type I, suggesting that the suppression of collagen type I was mainly post-translational.

TABLE 3

| | 100 nM |
|---|---|
| collagen I | 79.3 ± 13.5 |
| collagen III | 39.0 ± 13.5 |
| SM α-actin | 20.6 ± 15.4 |

EXAMPLE 3

Effect of Trichostatin A and Sodium Butyrate on the Cell Proliferation of Hepatic Stellate Cells Finally, the applicant examined the effects of Trichostatin A and sodium butyrate on proliferation of stellate cells, since high proliferative activity is one of the major features of myofibroblastic differentiation.

Cells were cultured in triplicate or quadruplicate in 24 well plates (Costar). Cells at day 2 were exposed to 0.01–1 mmol/L sodium butyrate or 1–100 nmol/L Trichostatin A for the 4 subsequent days. Culture medium and test compounds were replaced every day. At day 6 cells were trypsinized and counted in a hemocytometer.

Trichostatin A showed at 100 nmol/L a strong suppressive effect on proliferation. Table 4 summarizes these cell-count results.

TABLE 4

Cell-count results

| control | $10^{-7}$ M Trichostatin A | $10^{-8}$ M Trichostatin A | $10^{-9}$ M Trichostatin A |
|---|---|---|---|
| 23.7 ± 1.9 | 16.2 ± 1.0 | 22.0 ± 3.0 | 22.9 ± 1.0 |
| control | $10^{-3}$ M Butyrate | $10^{-4}$ M Butyrate | $10^{-5}$ M Butyrate |
| 23.9 ± 2.0 | 20.4 ± 0.2 | 22.2 ± 0.7 | 21.1 ± 2.0 |

Finally cells were cultured in triplicate or quadruplicate in 24 well plates. At day 4 cells were exposed tot 0.01–1 mmol/L sodium butyrate or 1–100 nmol/L Trichostatin A for 24 h. Subsequently, medium was changed and cells were further incubated for 20 h with the same concentrations of sodium butyrate or Trichostatin A in the presence of 10 μCi/ml [$^3$H]-thymidine (specific activity 25 Ci/mmol, 10 μCi/ml). Radioactivity incorporated into the 2% perchloric acid/95% ethanol/insoluble fraction was measured by scintillation counting. Parallel cultures incubated with [$^3$H]-thymidine in the presence of 10 mmol/L hydroxyurea provided the baseline value, which was subtracted from each measurement. Final data were normalized for cell number which was determined by trypsinization of parallel wells. Table 5 shows the results expressed in cpm/cell.

TABLE 5

[$^3$H]-thymidine incorporation

| control | $10^{-7}$ M Trichostatin A | $10^{-8}$ M Trichostatin A | $10^{-9}$ M Trichostatin A |
|---|---|---|---|
| 10.0 ± 0.8 | 1.3 ± 0 | 9.9 ± 0.4 | 9.6 ± 0.4 |
| control | $10^{-3}$ M butyrate | $10^{-4}$ M butyrate | $10^{-5}$ M butyrate |
| 9.9 ± 0.4 | 6.2 ± 0.2 | 9.5 ± 0.3 | 9.5 ± 0.2 |

EXAMPLE 4

Effect of Trichostatin A on the Cell Proliferation of Skin Fibroblasts

Skin fibroblasts were obtained from male Wistar rats (300–400 g) by the explant tehnique as described previously. All rats were fed ad libitum, and received humane care in compliance with the institution's guidelines for the care and use of laboratory animals in research. Cells were grown in Dulbecco's modified Eagle's medium with 10% fetal calf serum, and cultured at 37° C. in a humidified atmosphere with 5% $CO_2$ and 95% air. When the culture became confluent, cells were trypsinized and replated into 75 cm$^2$ culture flasks in a split ratio of 1:4. Experiments were performed using confluent cells between passage 5 and 9. Preliminary experiments have shown that under these conditions, skin fibroblasts had acquired the myofibroblast phenotype at the time of experiments, as evidenced by their large size, prominent stress fibers, and expression of smooth muscle α-actin.

Confluent cultures of skin fibroblasts were exposed to 1, 10 and 100 nmol/L trichostatin A for 24 h. For the TGF-$\beta_1$ experiment, cells were exposed to 5 ng/mL of human recombinant TGF-$\beta_1$ (Calbiochem) and/or 100 nmol/L trichostatin A for 24 h. After the initial 24 h exposure of these compounds, cells were metabolically labeled for 24 h with 50 μCi/mL of Trans $^{35}$S-label (specific activity of $^{35}$S-methionine>1,000 Ci/mmol, ICN Biomedicals, Costa Mesa, Calif.) in the presence of vitamin C (50 μg/mL) (Merck) and β-aminopropionitrile (64 μg/mL) (Sigma), while exposure to trichostatin A and/or TGF-$\beta_1$ was continued. Labeled media or cell layers were separately harvested and stored at −70° C. Protein synthesis was measured by trichloroacetic acid (TCA) precipitation. Equal counts ($10^6$ cpm) of labeled media or cell lysates were subjected to immunoprecipitation. Immunoprecipitation was performed using antibodies against collagen type I (Southern Biotechnology, Birmingham, Ala.), type III (Gift by Prof.Dr. D. Schuffan, Freie Univ. Berlin, Deutschland) or smooth muscle α-actin (clone 1A4, Sigma). After immunoprecipitation, proteins were separated by SDS-PAGE, gels were immersed in Amplify (Amersham, Little Charfort, UK) and dried, exposed to preflashed autoradiography film (Hyperfilm-MP, Amersham) or quantitatively analyzed by Phosphor-Imaging (Molecular Imager, GS-525, BioRad, USA).

Confluent cultures of fibroblasts were exposed to 100 nmol/L trichostatin A and/or 5 ng/mL TGF-$\beta_1$ for 24 h. Total RNA was extracted by the method of Chomczynski and Sacchi. Northern hybridization was performed as described, using $^{32}$P-labeled cDNA probes for rat procollagen $\alpha_1$(I) (1.6 kb Pst I fragment), rat procollagen $\alpha_1$(III) (0.5 kb Hind III/EcoRI fragment), and GAPDH (glyceraldehyde-3-phosphate dehydrogenase) (0.5 kb XbaI/HindIII fragment). For smooth muscle α-actin mRNA was used as described previously. The results were quantitated by Phosphor-Imaging and corrected for GAPDH.

The ratios of protein or mRNA levels of treated vs. controls were calculated for each experimental condition and expressed as means±standard deviation. For the protein study, correction was made for the difference, if any, in the trichloroacetic acid-precipitable counts. The number of experiments used to calculate a mean value was at least 3. The effect was considered statistically significant, when 1.0 did not belong to the 95% confidence interval of the treated/control ratio.

Then we metabolically labeled endogenously produced protein with $^{35}$S-methionine, and immunoprecipitated collagen type I and III using specific antibodies. The immunoprecipitated proteins were separated on SDS-PAGE and quantified by phosphor-imaging. We found that at 100 nmol/L, 10 nmol/L, and 1 nmol/l trichostatin A inhibited synthesis of collagen type I by 30%, 44%, and 17%, respectively (table 6, row 2). Synthesis of collagen type III was inhibited by 41%, 49%, and 10% at the same concentrations of trichostatin A (table 6, row 3). Thus, both collagen type I and III were inhibited by trichostatin A (p<0.05 for 100 nmol/L and p<0.01 for 10 nmol/L), with the maximal effect obtained at 10 nmol/L. Synthesis of smooth muscle α-actin, a marker for myofibroblast differentiation, was also inhibited by 37±18%, 36±8%, respectively, following exposure to 100 nmol/L and 10 nmol/L trichostatin A (table 6, row 4). These inhibitory effects of trichostatin A was selective, since over all protein synthesis as measured by TCA-precipitable counts was not affected.

Next we explored whether trichostatin A affected the fibrogenic actions of TGF-$\beta_1$ in skin fibroblasts. For this purpose, cells were exposed to TFG-$\beta_1$ (5 ng/mL) alone, trichostatin A (100 ng/mL) alone, or combination of TFG-$\beta_1$ (5 ng/mL) and trichostatin A (100 nmol/L). Collagen type I and III, and smooth muscle $\alpha$-actin were again immunoprecipitated, separated on SDS-PAGE and quantified by phosphor-imaging. As shown in table 7, exposure to TGF-$\beta_1$ stimulated synthesis of collagen type I and III 3.4 and 4.7 fold, respectively. Although stimulation occurred in every preparation of skin fibroblasts, the magnitude of stimulation varied from culture to culture ranging from 1.8 to 5.9 fold for collagen type I and from 2.5 to 8.0 fold for collagen type III. TGF-$\beta_1$, had a modest stimulating effect (1.8 fold increase) on the synthesis of smooth muscle $\alpha$-actin. Strikingly, the stimulating effect of TGF$\beta_1$ was largely abolished, when TGF-$\beta_1$ and trichostatin 1 were added simultaneously.

Finally, we explored at which level trichostatin A exerted its inhibitory effect on the collagen synthesis by skin fibroblasts. For this purpose we again exposed skin fibroblasts to trichostatin A and/or TGF-$\beta$1. After 24 hour exposure, total RNA was extracted and subjected to Northern hybridization analysis. The radioactivity was measured, corrected for GAPDH, and expressed as a ratio to the value of the control culture. As shown in table 8, TGF-$\beta_1$ (5ng/mL) increased gene expression of collagens type I, and III, and smooth muscle $\alpha$-actin 2.3 fold, 2.5 fold and 1.7 fold, respectively. Trichostatin A alone (100 nmol/L) had a modest suppressive effect on the mRNA levels of collagens type I and III and smooth muscle $\alpha$-actin. These data suggest that suppressive effect of trichostatin A occurs both at the transcriptional and posttranslational level.

The results of the above mentioned examples are summurized in table 6, 7 and 8.

TABLE 6

The effect of different concentrations of TSA at the protein level. Results are expressed as percentage of control value

|  | 100 nM | 10 nM | 1 nM |
|---|---|---|---|
| Collagen I | 70 +/− 13% | 56 +/− 11% | 83 +/− 11% |
| Collagen III | 59 +/− 18% | 51 +/− 11% | 90 +/− 14% |
| $\alpha$-SMA | 63 +/− 8% | 64 +/− 8% | 86 +/− 23% |

TABLE 7

The effect of TSA on inducing effect of TGF-$\beta$ at the protein level

|  | TGF-$\beta$ | TGF-$\beta$ + TSA | TSA |
|---|---|---|---|
| Collagen I | 347 ± 185% | 121 ± 39% | 70 ± 13% |
| Collagen III | 476 ± 273% | 86 ± 35% | 59 ± 18% |
| SMA | 175 ± 196% | 67 ± 6% | 63 ± 8% |

TABLE 8

The effect of TSA on the inducing effect of TGF-$\beta$ at the mRNA level

|  | TGF-$\beta$ | TGF-$\beta$ + TSA | TSA |
|---|---|---|---|
| Collagen I | 231 ± 89% | 132 ± 49% | 84 ± 14% |
| collagen III | 253 ± 94% | 180 ± 51% | 74 ± 10% |
| SMA | 171 ± 61% | 114 ± 24% | 85 ± 16% |

The results in this application indicate that histone deacetylase inhibitors provide a novel therapeutic potential in the treatment of fibro-proliferative diseases.

In conclusion, we have demonstrated that two unrelated histone deacetylase inhibitors are active antifibronics compounds as two well known experimental models of fibrosis, i.e. hepatic fibrosis and skin fibrosis.

The invention further relates to a method for the treatment of humans or animals afflicted with fibrosis, comprising administering to said subject an effective amount of a histone deacetylase inhibitor in particular Trichostatin A or a pharmaceutically acceptable salt thereof and optionally a suitable excipient.

We claim:

1. A pharmaceutical composition for the treatment of fibrosis comprising a histone deacetylase inhibitor and a pharmaceutically acceptable carrier wherein the histone deacetylase inhibitor is trichostatin A or a pharmaceutically acceptable salt thereof.

2. A pharmaceutical composition for the treatment of fibrosis comprising a histone deacetylase inhibitor and a pharmaceutically acceptable carrier wherein the histone deacetylase inhibitor is present in an amount from 0.1 to 50% by weight of the composition.

3. A pharmaceutical composition for the treatment of fibrosis comprising a histone deacetylase inhibitor and a pharmaceutically acceptable carrier wherein the composition comprises from 0.05 to 100 mg of the histone deacetylase inhibitor.

4. The composition according to claim 1 wherein the pharmaceutical salt is selected from the group consisting of an alkali metal salt, an alkaline earth metal salt, or a salt with an organic base.

5. The composition according to claim 4 wherein the pharmaceutical salt is selected from the group consisting of a sodium salt, a potassium salt, a calcium salt, a magnesium salt, an ammonium salt, a triethylamine salt, and an ethanolamine salt.

6. Method for treating fibrosis comprising administering to humans or animals in need of an anti-fibrotic treatment a therapeutically effective amount of a pharmaceutical composition comprising a histone deacetylase inhibitor and a pharmaceutically acceptable carrier.

7. The method for treating fibrosis according to claim 6 wherein the pharmaceutical composition is administered non-orally.

8. The method for treating fibrosis according to claim 7 wherein the composition is a creme, an ointment, an injection solution, a drip infusion, or suppositories.

9. The method for treating fibrosis according to claim 6 wherein the histone deacetylase inhibitor is trichostatin A or a pharmaceutically acceptable salt thereof.

10. The method for treating fibrosis according to claim 6 wherein the histone deacetylase inhibitor is sodium butyrate.

11. The method for treating fibrosis according to claim 6 wherein the histone deacetylase inhibitor is present in an amount from 0.1 to 50% by weight of the composition.

12. The method for treating fibrosis according to claim 6 wherein the composition comprises from 0.05 to 100 mg of the histone deacetylase inhibitor.

13. The method for treating fibrosis according to claim 12 wherein the pharmaceutical salt is selected from the group consisting of an alkali metal salt, an alkaline earth metal salt, or a salt with an organic base.

14. The method for treating fibrosis according to claim 13 wherein the pharmaceutical salt is selected from the group consisting of a sodium salt, a potassium salt, a calcium salt, a magnesium salt, an ammonium salt, a triethylamine salt, and an ethanolamine salt.

* * * * *